(12) United States Patent
Mayan et al.

(10) Patent No.: US 6,506,404 B1
(45) Date of Patent: Jan. 14, 2003

(54) RELEASE OF IBUPROFEN FROM HOT MELT ADHESIVE COMPOSITIONS THROUGH ADDITION OF PHARMACEUTICAL AUXILIARIES

(75) Inventors: Robert Mayan, Buxtehude (DE); Matthias Wasner, Hamburg (DE); Peter Philipp, Barsbüttel (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/363,212

(22) Filed: Jul. 29, 1999

(30) Foreign Application Priority Data

Jul. 31, 1998 (DE) .......................... 198 34 496

(51) Int. Cl.⁷ ................................. A61K 9/70
(52) U.S. Cl. .................. 424/449; 424/448; 514/570; 604/307
(58) Field of Search ................ 424/449, 448; 514/570; 604/307

(56) References Cited

U.S. PATENT DOCUMENTS

| | | | |
|---|---|---|---|
| 4,555,524 A | 11/1985 | Gruber et al. | 514/570 |
| 4,837,025 A | 6/1989 | Guillemet et al. | 424/448 |
| 5,527,536 A | 6/1996 | Merkle et al. | 424/448 |
| 5,702,720 A | 12/1997 | Effing et al. | 424/448 |

FOREIGN PATENT DOCUMENTS

| | | | |
|---|---|---|---|
| EP | 0305757 | 3/1989 | |
| EP | 0827741 | 3/1998 | ............ A61K/9/70 |
| WO | 9300058 | 1/1993 | |
| WO | 9423713 | 10/1994 | .......... A61K/31/19 |

*Primary Examiner*—Michael G. Hartley
*Assistant Examiner*—Michael A. Williamson
(74) *Attorney, Agent, or Firm*—Norris McLaughlin & Marcus

(57) ABSTRACT

Use of auxiliaries to improve the release of ibuprofen from hot melt adhesive compositions.

9 Claims, No Drawings

RELEASE OF IBUPROFEN FROM HOT MELT ADHESIVE COMPOSITIONS THROUGH ADDITION OF PHARMACEUTICAL AUXILIARIES

The invention relates to the improved release of active ingredients from hot melt adhesive compositions through addition of pharmaceutical auxiliaries.

In the formulation of medicinal products for topical administration of active ingredients, the choice of the auxiliaries has crucial importance.

Thus, it is known that there is a connection between the solubility of an active ingredient in a vehicle and its release from this vehicle. Application of an active ingredient-containing vehicle to the skin results in an active ingredient partition equilibrium between vehicle and skin being set up. The position of this equilibrium is determined by the solubility in the two phases and is described by the partition coefficient $P_s$.

According to Fick's 1st law, the following applies to the flux of a dissolved substance from a vehicle into the skin:

$$J_s = \frac{P_s C_i D_i}{h}$$

where $J_s$ is the flux, $P_s$ is the partition coefficient, $C_i$ is the concentration of the active ingredient in the vehicle, $D_i$ is the diffusion coefficient and h is the thickness of the skin.

According to Hildebrand and Scott, the following equation applies to the solubility of a polymer in a solvent:

$$\Delta H_m = V_m \phi_1 \phi_2 (\delta_1 - \delta_2)^2$$

with $\Delta H_m$ enthalpy of mixing, $V_m$ total volume of the mixture, $\Phi$ volume content of the components and $\delta$ solubility parameter,
where the solubility is good when the parameters are close to identical and thus the term $(\delta_1 - \delta_2)$ is small.

A difference of $\delta_1 - \delta_1 < 2$ indicates expected solubility.

Hildebrand's solubility parameter is defined as the total of all the intramolecular attractive forces for a substance and can be measured by various methods. A general discussion of the solubility parameter concept can be read in a number of publications; as an example, Vaughan, C. D., Journal of the Society of Cosmetic Chemists 36, 319–333 (1985) may be mentioned here.

It is possible to derive from these equations according to Sloan, K. B. et al, Journal of Pharmaceutical Sciences, 75, 744 (1986) the following expression for the partition equilibrium of an active ingredient between vehicle and skin:

$$\ln P_s = \frac{(\delta_i - \delta_v)^2 V_i \phi_v^2}{RT} - \frac{(\delta_i - \delta_s)^2 V_i \phi_s^2}{RT} = \ln \frac{C_i^{skin}}{C_i^{vehicle}}$$

$V_i$ molar volume of the active ingredient
$\delta_i$ active ingredient solubility parameter
$\delta_v$ vehicle solubility parameter
$\delta_s$ skin solubility parameter The release of a low molecular weight substance from a polymeric matrix is determined by complex interplay of specific interactions of all the components. According to the above equation, the concentration of active ingredient in the skin is high when the solubility in the skin is high and the solubility in the vehicle is low. Accordingly, it is possible to alter the release of an active ingredient from a vehicle by adjusting the solubility parameter $\delta_v$ of this vehicle.

Since Hildebrand's solubility parameter $\delta$ is a material constant, it further follows from this equation that a specific modification of the vehicle is necessary for each active ingredient. It is not possible to draw conclusions by analogy within a group of chemical substances or family of active ingredients because of the significant differences in the $\delta$ values. This is made clear for example by the values for chemically closely related auxiliaries such as cetyl alcohol ($\delta=8.94$), lauryl alcohol ($\delta=9.51$) and capryl alcohol ($\delta=10.09$) or else ethylene glycol ($\delta=14.50$), diethylene glycol ($\delta=13.61$) and triethylene glycol ($\delta=12.21$).

As is evident, inter alia from U.S. Pat. No. 4,555,524, the beneficial use of auxiliaries for distinctly improved release of an active ingredient is known for topical administration forms such as creams or ointments. This achieves, by dissolving ibuprofen in a combination of pharmaceutical auxiliaries, increased release of the active ingredient compared with formulations containing the undissolved active ingredient. Deliberate adjustment of the solubility parameter $\delta_v$ of the vehicle for optimal release of ibuprofen is not described therein. In addition, the amounts of auxiliary employed are so large that it is not possible to produce adhesive administration forms with them.

The strategy described above is used only in a few cases of so-called drug-in adhesive systems, that is to say active ingredient-containing plasters containing the medicinal substance in the adhesive composition.

Hot melt adhesive compositions make it possible to avoid the disadvantages associated with the use of solvents which is necessary in conventional active ingredient-containing adhesive compositions. Mention should here be made of the harmfulness of most organic solvents, high industrial expenditures for extraction and recovery, high costs for the required high-purity solvents and, in particular, very high expenditure for removing solvent residues from the matrix.

The advantages of hot melt adhesive compositions for producing active ingredient-containing adhesive compositions have been described in the patent literature for some years now (see, for example, EP 0 305 757 A1).

The targeted optimization of the solubility of an active ingredient in a matrix is not known for hot melt adhesive compositions based on polystyrene block copolymers.

U.S. Pat. No. 5,527,536 describes active ingredient-containing hot melt adhesive compositions based on polystyrene block copolymers, especially polystyrene block copoly(ethylene/butylene) block polystyrene (SEBS). These compositions contain besides SEBS tackifiers and antioxidants. The use and benefits of added pharmaceutical auxiliaries is not described.

For hot melt adhesive compositions based on ethylene/vinyl acetate copolymers, optimization of release of active ingredients is described in U.S. Pat. No. 4,837,025. Fatty acid esters with polyalcohols are used here.

WO 93/00058 describes the optimization of active ingredient-containing adhesive compositions by application of the principles described above, with the solubility parameter $\delta_v$ being altered by mixing two polymeric adhesive compositions with different solubility parameters, preferably a silicone adhesive composition and an acrylate adhesive composition. Low molecular weight auxiliaries are not employed to adjust the $\delta_v$.

U.S. Pat. No. 5,702,720 describes an active ingredient-containing plaster which contains flurbiprofen dissolved in an acrylate adhesive composition. Isopropyl myristate which is likewise present acts as promoter which enhances penetration of the active ingredient through the skin. This low molecular weight auxiliary is evidently not employed to optimize the solubility in the vehicle.

WO 94/23713 describes anti-inflammatory medicinal products based on phenylpropionic acids and phenylacetic acids for topical administration which contain combinations of lipophilic and hydrophilic auxiliaries. No statements are made about the mode of action and function of these auxiliaries.

Adjustment of the solubility parameter $\delta_v$ of the vehicle by adding lipophilic and hydrophilic auxiliaries is evidently not intended and would be complicated and laborious. In addition, the effects of the different auxiliaries on $\delta_v$ would be in contrary directions and would cancel each other out.

EP 0 827 741 A2 discloses that the release of ketoprofen from adhesive vehicles can be improved by adding auxiliaries. For example, polyisobutylenes dissolved in hexane/toluene are described as the basis for the adhesive composition.

Ibuprofen is (±)-2-(4-isobutylphenyl)propionic acid ($C_{13}H_{18}O_2$; $M_R$ 206.28; melting point 75 to 77° C.) with the general formula

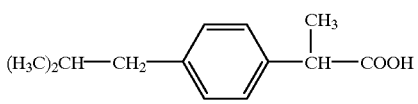

(according to Römpp Lexikon Chemie, version 1.3, Stuttgart/New York: Georg Thieme Verlag 1997). Ibuprofen is a known active ingredient with analgesic and anti-inflammatory properties and is therefore employed for soft-tissue rheumatism and inflammatory joint disorders. The active ingredient is mostly used in the form of tablets or suppositories. Oral administration may, however, lead to side effects such as nausea, vomiting, dizziness and headaches. Ibuprofen must for this reason not be taken by patients with gastric ulcers.

After topical application, the active ingredient reaches the target without previously being metabolized in the liver. This makes it possible to avoid disadvantages such as the so-called first-pass effect and side effects associated with an oral or rectal administration of ibuprofen. Release of the active ingredient from an adhesive matrix has further advantages compared with conventional topical administration forms such as creams or ointments. The active ingredient is released continuously from the matrix and is not administered in single doses. If unwanted side effects occur, the active ingredient-containing plaster can simply be removed and thus delivery of ibuprofen be stopped.

It is an object of the invention to avoid the disadvantages known from the prior art and thus improve the release of ibuprofen from hot melt adhesive compositions.

This object is achieved by adding low molecular weight auxiliaries to hot melt adhesive compositions to achieve optimized release by altering the solubility parameter of the vehicle $\delta_v$.

The auxiliaries preferably used in the hot melt adhesive compositions are fatty acid esters $C_8-C_{18}$ with short-chain alcohols or fatty alcohols.

The term fatty alcohols is the collective term for linear, saturated or unsaturated primary alcohols (1-alkanols) with 6 to 22 carbon atoms which are obtainable by reduction of triglycerides, fatty acids or fatty acid methyl esters.

Fatty alcohols are neutral, colourless, high-boiling, oily liquids or soft colourless compounds which are of low solubility or insoluble in water but readily soluble in alcohol and ether.

The table below indicates physicochemical data for fatty alcohols (from Rompp Lexikon Chemie, version 1.3, Stuttgart/New York: Georg Thieme Verlag 1997).

TABLE

Physicochemical data for fatty alcohols

| Alcohol | Formula | $M_R$ | m.p. ° C. | b.p. ° C./kPa |
|---|---|---|---|---|
| 1-hexanol (Capric alcohol) | $C_6H_{14}O$ | 102.18 | −51.6 | 157.2 |
| 1-heptanol (enanthic alcohol) | $C_7H_{16}O$ | 116.20 | −30.0 | 177 |
| 1-octanol (capryl alcohol) | $C_8H_{18}O$ | 130.23 | −16.3 | 194.5 |
| 1-nonanol (pelargonic alcohol) | $C_9H_{20}O$ | 144.26 | | 212 |
| 1-decanol (capric alcohol) | $C_{10}H_{22}O$ | 158.28 | −7.0 | 229 |
| 1-undecanol | $C_{11}H_{24}O$ | 172.31 | 16.3 | 131/2.0 |
| 10-undecen-1-ol | $C_{11}H_{22}O$ | 170.30 | −2 | 133/2.1 |
| 1-dodecanol (lauryl alcohol) | $C_{12}H_{26}O$ | 186.34 | 23.8 | 150/2.7 |
| 1-tridecanol | $C_{13}H_{28}O$ | 200.36 | | 155/2.0 |
| 1-tetradecanol (myristyl alcohol) | $C_{14}H_{30}O$ | 214.39 | 38.0 | 167/2.0 |
| 1-pentadecanol | $C_{15}H_{32}O$ | 228.42 | 44.0 | |
| 1-hexadecanol (cetyl alcohol) | $C_{16}H_{34}O$ | 242.45 | 49.3 | 190/2.0 |
| 1-heptadecanol | $C_{17}H_{36}O$ | 256.47 | 54.0 | 308 |
| 1-octadecanol (stearyl alcohol) | $C_{18}H_{38}O$ | 270.50 | 59.0 | 210/2.0 |
| 9-cis-octadecen-1-ol (oleyl alcohol) | $C_{18}H_{36}O$ | 268.48 | −7.5 | 209/2.0 |
| 9-trans-octadecen-1-ol (elaidyl alcohol) | $C_{18}H_{36}O$ | 268.48 | 36.5 | 216/2.4 |
| 9-cis-octadecen-1,12-diol (ricinoleic alcohol) | $C_{18}H_{36}O_2$ | 284.48 | | 182/0.07 |
| all-cis-9,12-octadecadien-1-ol (linoleyl alcohol) | $C_{18}H_{34}O$ | 266.47 | −5 | 153/0.4 |
| all-cis-9,12,15-octadecatrien-1-ol (linolenyl alcohol) | $C_{16}H_{32}O$ | 264.45 | | 133/0.3 |
| 1-nonadecanol | $C_{19}H_{40}O$ | 284.53 | 62 | 167/0.04 |
| 1-eicosanol (arachidyl alcohol) | $C_{20}H_{42}O$ | 298.55 | 65.5 | 220/0.4 |
| 9-cis-eicosen-1-ol (gadoleyl alcohol) | $C_{20}H_{40}O$ | 296.54 | | 209/2.0 |
| 5,8,11,14-eicosatetraen-1-ol | $C_{20}H_{34}O$ | 290.49 | | |
| 1-heneicosanol | $C_{21}H_{44}O$ | 312.58 | 69.5 | |
| 1-docosanol (behenyl alcohol) | $C_{22}H_{46}O$ | 326.61 | 73.5 | 180/0.03 |
| 1-3-cis-docosen-1-ol (erucyl alcohol) | $C_{22}H_{44}O$ | 324.59 | 34.5 | 241/1.3 |
| 1-3-trans-docosen-1-ol (brassidyl alcohol) | $C_{22}H_{44}O$ | 324.59 | 53.5 | 241/1.1 |

Further preferred auxiliaries are esters and ethers of polyethylene glycol 6 to −12 with $C_8-C_{18}$ fatty alcohols.

Polyethylene glycols mean polyalkylene glycols which belong to the class of polyethers and have the general formula:

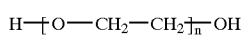

Polyethylene glycols are produced industrially by a base-catalysed polyaddition of ethylene oxide (oxirane) usually in systems containing small amounts of water, with ethylene glycol as starter molecule. They have molecular weights in the region of about 200–5,000,000 g/mol, corresponding to degrees of polymerization n of about 5 to >100,000.

Further preferred auxiliaries are propylene glycol mono- and diesters with $C_8-C_{18}$ fatty acids.

Further preferred auxiliaries are glycerol mono-, di- and triesters with $C_8-C_{18}$ fatty acids.

Further preferred auxiliaries are $C_8$–$C_{18}$ fatty alcohols and glycols such as propylene glycol and/or polyethylene glycol.

The content of auxiliaries in the hot melt adhesive compositions is preferably from 1 to 20% by weight, in particular 2 to 15% by weight.

In another preferred embodiment, the hot melt adhesive composition is a polystyrene block copolymer hot melt adhesive composition, very particularly preferably a polystyrene block copoly(ethylene/butylene) block polystyrene hot melt adhesive composition.

It is possible and advantageous to employ as hot melt adhesive compositions thermoplastic hot melt contact adhesive compositions based on natural and synthetic rubbers and other synthetic polymers such as acrylates, methacrylates, polyurethanes, polyolefins, polyvinyl derivatives, polyesters or silicones. Additives such as adhesive resins, plasticizers, stabilizers and other auxiliaries can be added if necessary.

The softening point of the hot melt adhesive compositions should be higher than 50° C. because the application temperature is usually at least 90° C., preferably between 120° C. and 150° C., or 180° C. and 240° C. for silicones.

Hot melt contact adhesive compositions based on block copolymers are distinguished in particular by the wide variety of possible variations thereof, since the necessary adhesion to the skin appropriate for the function is ensured even at critical points on the human locomotor system by the specific choice of the tackifiers, the plasticizers and the degree of polymerization and the molecular weight distribution of the components employed.

The high shear strength of the hot melt contact adhesive composition based on block copolymers is achieved through the high cohesivity of the polymer. The good tack results from the range of tackifiers and plasticizers employed.

For particularly strongly adhesive systems, the hot melt contact adhesive composition is preferably based on block copolymers, in particular A-B, A-B-A block copolymers or mixtures thereof. Phase A is mainly polystyrene or derivatives thereof, phase B contains ethylene, propylene, butylene, butadiene, isoprene or mixtures thereof, in this case particularly preferably ethylene and butylene or mixtures thereof.

The two phases A and B are not miscible so that domains of polystyrene blocks and copoly(ethylene/butylene) blocks form in the solid state.

Polystyrene is below its glass transition temperature and thus contributes to the high shear strength, whereas copoly (ethylene/butylene) blocks are above their glass transition temperature and show elastic behaviour.

The glass transition temperature is the temperature at which amorphous or partly crystalline polymers change from the liquid or rubbery elastic state into the energy elastic or glassy state or vice versa (Römpp Chemie-Lexikon, 9th ed. volume 2, page 1587, Georg Thieme Verlag Stuttgart—New York, 1990). It corresponds to the maximum of the temperature function at a preset rate.

A relatively low glass transition temperature is necessary in particular for medical applications.

Specific mixing of di-block and tri-block copolymers is particularly advantageous, and a content of di-block copolymers of less than 80% by weight is preferred.

In an advantageous embodiment, the hot melt contact adhesive composition has the composition indicated below:

10% by weight to 90% by weight of block copolymers,
5% by weight to 80% by weight of tackifiers such as oil, waxes, resins and/or mixtures thereof, preferably mixtures of resins and oils,
less than 60% by weight of plasticizers,
less than 15% by weight of additives,
less than 5% by weight of stabilizers,
0.01% by weight to 10% by weight of active ingredient or active ingredients.

The aliphatic or aromatic oils, waxes and resins used as tackifiers are preferably hydrocarbon oils, waxes and resins, and the oils such as paraffin hydrocarbon oils or the waxes such as paraffin hydrocarbon waxes, have a beneficial effect on the adhesion to the skin due to their consistency. These additives are moreover used to adjust the adhesive properties and the stability. Further stabilizers and other auxiliaries are employed where appropriate.

Filling of the adhesive composition with mineral fillers, fibres, or hollow or solid microbeads is possible.

The hot melt contact adhesive composition has a softening point above 50° C., preferably from 70° C. to 220° C., very particularly preferably from 75° C. to 140° C.

The hot melt contact adhesive compositions are preferably adjusted so that they have at a rate of 0.1 rad/s a dynamic complex glass transition temperature below 10° C., preferably from 0° C. to –30° C., very particularly preferably from –6° C. to –25° C.

Plasters in particular are subject to strict demands concerning the adhesive properties. For ideal application, the hot melt contact adhesive composition should have a high degree of tack. The strength of adhesion to the skin should be appropriate for the function. It is also necessary for the hot melt contact adhesive composition to have high shear strength so that no residues of composition remain on the skin on detachment of the plaster. If relatively large amounts of pharmaceutical auxiliaries are added, the high shear strength can be maintained by reducing or eliminating the plasticizers.

The product properties such as tack, glass transition temperature and shear resistance can be quantified well by means of a dynamic mechanical rate measurement. A shear stress-control rheometer is used for this purpose.

The results of this method of measurement provide information on the physical properties of a substance through taking the viscoelastic content into account. This entails the hot melt contact adhesive composition being caused to vibrate at a preset temperature between two plane-parallel plates at variable rates and with little deformation (linear viscoelastic range). The quotient (Q=tan δ) between the loss modulus (G" viscous portion) and the storage modulus (G' elastic portion) is determined with computer assistance via a recording control unit.

$$Q = \tan \delta = G''/G'$$

A high rate is chosen for the subjective sensation of tack, and a low rate is chosen for the shear strength.

A high numerical value means better tack and less good shear resistance.

Hot melt contact adhesive compositions preferred according to the invention are those for which the ratio of the viscous portion to the elastic portion at a rate of 100 rad/s at 25° C. is greater than 0.7, preferably 1.0 to 5.0, or those for which the ratio of the viscous portion to the elastic portion at a rate of 0.1 rad/s at 25° C. is less than 0.6, preferably between 0.4 and 0.02, very particularly preferably between 0.3 and 0.1.

In order to ensure use appropriate for the function, the hot melt adhesive compositions can be formed, in particular preferably foamed with inert gases such as nitrogen, carbon dioxide, noble gases, hydrocarbons or air or mixtures thereof. In some cases, foaming additionally by thermal decomposition of gas-evolving substances such as azo, carbonate and hydrazide compounds has proved suitable.

The degree of foaming, that is to say the gas content, should be at least about 5% by volume and can extend up to about 85% by volume. In practice, values from 10% by volume to 75% by volume, preferably 50% by volume, have proved very suitable. Use of relatively high temperatures of about 100° C. and a comparatively high internal pressure results in very open-cell firmed adhesive foam layers which have particularly high permeability to air and water vapour.

The inventive concept additionally embraces active ingredient-containing plasters with a substrate material and, applied at least partially thereto, a hot melt adhesive composition, which are distinguished in that the hot melt adhesive composition contains ibuprofen.

The quantitative concentrations of ibuprofen in the hot melt adhesive composition are preferably between 0.01 and 50% by weight, preferably from 0.1 to 20% by weight.

Suitable substrate materials for the hot melt adhesive composition s are all rigid and elastic flat materials made of synthetic and natural raw materials. Preferred substrate materials are those which, after application of the adhesive composition, can be employed in such a way that they comply with the properties of a dressing appropriate for the function.

Examples of substrates which are mentioned are wovens, nets, lays, nonwovens, laminates, networks, films, foams and papers. It is furthermore possible for these materials to be pre- and/or post-treated. Customary pretreatments are corona and making water-repellent; common post-treatments are calendering, conditioning, laminating, punching and covering.

Finally, the plaster can, after the coating process, be covered with an adhesiverepellent substrate material such as siliconized polyester film, or be provided with a wound cover or a cushion.

The plasters are then punched out in the required size.

The plaster according to the invention has a strength of adhesion to steel of at least 1.0 N/cm preferably a strength of adhesion between 1.5 N/cm and 6.0 N/cm, very particularly preferably a strength of adhesion between 1.5 N/cm and 6.0 N/cm. Higher or lower strengths of adhesion can be reached on other substrates.

The substances employed according to the invention as auxiliaries are widely used in pharmaceutical and cosmetic products, and in foodstuffs, and are distinguished by excellent, proven tolerability.

Surprisingly, it is possible to incorporate the pharmaceutical auxiliaries described into hot melt adhesive compositions without a significant reduction in the shear strength. In addition, the tested auxiliaries allow the release to be greatly improved.

The invention is further described hereinafter by means of several examples without restricting it thereby.

EXAMPLES

Production of Ibuprofen-containing SEBS Adhesive Compositions with Addition of Auxiliaries The active ingredient-free adhesive composition is the SEBS adhesive composition designated E94 from HB Fuller GmbH, D-21335 Lüneburg. The active ingredient ibuprofen is dissolved in ethyl oleate at 60° C. and fed into the adhesive composition which is melted in a heated kneader. The components employed are homogenized at a temperature of 90° C. over a period of 3 h.

The adhesive composition produced in this way is fed molten into a coating unit and applied to siliconized paper at a rate of 300 g/m$^2$. The substrate material is then laminated on.

Determination of Release of Active Ingredient on Pig Skin

The active ingredient-containing adhesive compositions produced were tested for release of the active ingredient as follows:

The release was determined on excised pig skin (stratum corneum, epidermis, dermis). For this purpose, pieces of plaster of suitable size were stuck onto the stratum corneum. During the test, the underside of the skin on the dermis side was flushed by a receptor phase. After the preset time, the pieces of plaster were removed and the remaining active ingredient content was determined. For this purpose, the adhesive composition was dissolved and the solution was analyzed by HPLC. Unapplied pieces of plaster were investigated in the same way. The release results from the difference in the active ingredient contents.

The release results obtained for ibuprofen demonstrate the effect of the added auxiliaries. In the case of the SEBS adhesive composition investigated by way of example, the release could be increased from nonmeasurable (without addition of auxiliary) to as much as 185 µg/cm$^2$ 24 h (by addition of ethyl oleate). Further results are to be found in Table 1.

TABLE 1

Release of ibuprofen from SEBS hot melt adhesive compositions

| Adhesive composition used | Pharmaceutical auxiliary Release Pig skin | µg/cm$^2$*24h |
|---|---|---|
| SEBS E94 | — | not measurable |
| SEBS E94 | ethyl oleate (5%) | 185 |
| SEBS E94 | 2-octyldodecyl myristate (5%) | 116 |
| SEBS E94 | cetostearyl isononanoate (5%) | 102 |
| SEBS E94 | cetyl palmitate (5%) | 155 |
| SEBS E94 | polyethylene glycol 400 monostearate (5%) | 140 |
| SEBS E94 | polyethylene glycol 6000 (5%) | 46 |
| SEBS E94 | cocoglycerides (5%) | 134 |
| SEBS E94 | polyethylene glycol 400 (5%) | 103 |
| SEBS E94 | 1-octadecanol (5%) | 140 |
| SEBS E94 | glycerol monooleate (5%) | 100 |
| SEBS E94 | propylene glycol (5%) | 134 |
| SEBS E94 | 2-octyldodecanol (5%) | 63 |
| SEBS E94 | polyethylene glycol 450 monododecyl ether (5%) | 153 |

The active ingredient is homogeneously dispersed in the hot melt adhesive composition in a heated homogenizer such as, for example, heated mixer, heated kneader, roll systems or screw systems. Addition of the active ingredient to the molten adhesive composition preferably takes place in a form dissolved in the auxiliary, but it can also take place in pure form.

What is claimed is:

1. A method for improving the release of ibuprofen from hot melt adhesive compositions which comprise adding low molecular weight auxiliaries to said hot melt adhesive compositions, wherein said low molecular weight auxiliaries are selected from the group consisting of:

a) esters and ethers of polyethylene glycol 6 to −12 with $C_8$–$C_{18}$ fatty alcohols, b) propylene glycol mono- and diesters with $C_8$–$C_{18}$ fatty acids, c) glycerol mono-, di- and triesters with $C_8$–$C_{18}$ fatty acids, and d) $C_8$–$C_{18}$ fatty alcohols and glycols.

2. Method according to claim 1, wherein the auxiliaries are esters and ethers of polyethylene glycol 6 to –12 with $C_8$–$C_{18}$ fatty alcohols.

3. Method according to claim 1, wherein the auxiliaries are propylene glycol mono- and diesters with $C_8$–$C_{18}$ fatty acids.

4. Method according to claim 1, wherein the auxiliaries are glycerol mono-, di- and triesters with $C_8$–$C_{18}$ fatty acids.

5. Method according to claim 1, wherein the auxiliaries are $C_8$–$C_{18}$ fatty alcohols and glycols.

6. Method according to claim 1, wherein the contents of the auxiliaries in the hot melt adhesive composition are from 1 to 20% by weight.

7. Method according to claim 1, wherein the hot melt adhesive composition is a polystyrene block copolymer hot melt adhesive composition.

8. Active ingredient-containing plasters comprising a substrate material, and, at least partially applied thereto, a hot melt adhesive composition, wherein the hot melt adhesive composition contains ibuprofen and an auxiliary selected from the group consisting of:

a) esters and ethers of polyethylene glycol 6 to –12 with $C_8$–$C_{18}$ fatty alcohols b) propylene glycol mono- and diesters with $C_8$–$C_{18}$ fatty acids, c) glycerol mono-, di- and triesters with $C_8$–$C_{18}$ fatty acids, and d) $C_8$–$C_{18}$ fatty alcohols and glycols.

9. Active ingredient-containing plasters according to claim 8, wherein the hot melt adhesive composition contains ibuprofen in an amount of from 0.01 to 50% by weight.

* * * * *